United States Patent
Souza et al.

(10) Patent No.: US 9,416,140 B2
(45) Date of Patent: Aug. 16, 2016

(54) PROCESS FOR PREPARATION OF 3-((2S,5S)-4-METHYLENE-5-(3-OXOPROPYL)TETRAHYDROFURAN-2-YL)PROPANOL DERIVATIVES AND INTERMEDIATES USEFUL THEREOF

(71) Applicant: ALPHORA RESEARCH INC., Mississauga (CA)

(72) Inventors: Fabio E. S. Souza, Mississauga (CA); Jason A. Bexrud, Toronto (CA); Ricardo Orprecio, Mississauga (CA); Boris Gorin, Oakville (CA)

(73) Assignee: ALPHORA RESEARCH INC., Mississauga (CA)

( * ) Notice: Subject to any disclaimer, the term of this patent is extended or adjusted under 35 U.S.C. 154(b) by 0 days.

(21) Appl. No.: 14/882,845

(22) Filed: Oct. 14, 2015

(65) Prior Publication Data

US 2016/0031900 A1 Feb. 4, 2016

Related U.S. Application Data

(62) Division of application No. 14/365,168, filed as application No. PCT/CA2012/050897 on Dec. 14, 2012, now Pat. No. 9,174,956.

(60) Provisional application No. 61/576,649, filed on Dec. 16, 2011.

(51) Int. Cl.
| | |
|---|---|
| *C07D 493/04* | (2006.01) |
| *C07D 493/10* | (2006.01) |
| *C07D 493/22* | (2006.01) |
| *C07D 493/08* | (2006.01) |
| *C07D 307/12* | (2006.01) |
| *C07D 307/20* | (2006.01) |
| *C07D 307/28* | (2006.01) |

(52) U.S. Cl.
CPC ............ *C07D 493/22* (2013.01); *C07D 307/12* (2013.01); *C07D 307/20* (2013.01); *C07D 307/28* (2013.01); *C07D 493/04* (2013.01); *C07D 493/08* (2013.01); *C07D 493/10* (2013.01); *Y02P 20/55* (2015.11)

(58) Field of Classification Search
CPC .. C07D 493/04; C07D 493/10; C07D 493/22; C07D 493/08; C07D 307/12; C07D 307/20; C07D 307/28
See application file for complete search history.

(56) References Cited

U.S. PATENT DOCUMENTS

| 5,436,238 A | 7/1995 | Kishi et al. |
| 6,214,865 B1 | 4/2001 | Littlefield et al. |
| 2004/0192885 A1 | 9/2004 | Sharma et al. |

FOREIGN PATENT DOCUMENTS

| CA | 2166898 | 9/2004 |
| WO | 93/17690 | 9/1993 |
| WO | 99/65894 | 12/1999 |
| WO | 2005118565 | 12/2005 |
| WO | 2009/124237 | 10/2009 |
| WO | 2013/078559 | 6/2013 |
| WO | 2013/097042 | 7/2013 |
| WO | 2013/142999 | 10/2013 |
| WO | 2014/183211 | 11/2014 |

OTHER PUBLICATIONS

Knapp et al., 2002, caplus an 2002:73869.*
Jordaan et al., 1979, caplus an 1979:523936.*
Choi et al., "Synthetic studies on the marine natural product halichondrins", Pure Appl. Chem., vol. 75, No. 1, pp. 1-17, 2003, Massachusetts.
Choi et al., "Asymmetric Ni(II)/Cr(11)—Mediated Coupling Reaction: Catalytic Process", Organic Letters, vol. 4, No. 25, pp. 4435-4438, 2002, Massachusetts.
Cook et al., "Total Synthesis of (--)-Exiguolide", Organic Letters, vol. 12, No. 4, pp. 744-747, 2010, France.
Dong et al., "New Syntheses of E7389 C14-C35 and Halichondrin C14-C38 Building Blocks: Reductive Cyclization and Oxy-Michael Cyclization Approaches", J. Am. Chem. Soc., vol. 131, pp. 15642-15646, 2009, Massachusetts.
Guo et al., "Toolbox Approach to the Search for Effective Ligands for Catalytic Asymmetric Cr-Mediated Coupling Reactions", J. Am. Chem. Soc., vol. 131, pp. 15387-15393, 2009, Massachusetts.
Han et al., "Iridium-Catalyzed anti-Diastereo- and Enantioselective Carbonyl (Trimethylsilyl)allylation from the Alcohol of Aldehyde Oxidation Level", J. Am. Chem. Soc., vol. 132, pp. 9153-9156, 2010, Texas.
Han et al., Supporting Information to "Iridium-Catalyzed anti-Diastereo- and Enantioselective Carbonyl (Trimethylsilyl) allylation from the Alcohol of Aldehyde Oxidation Level", J. Am. Chem. Soc., vol. 132, pp. 9153-9156, 2010, Texas.
Jackson et al., "A Total Synthesis of Norhalichondrin B", Angewandte Chemie, vol. 48, No. 13, pp. 1-132, 2009, Colorado.
Jackson et al., "The Halichondrins and E7389", Chem. Rev., vol. 109, pp. 3044-3079, 2009, Colorado.
Jiang et al., "A Practical Synthesis of the F-Ring of Halichondrin B via Ozonolytic Desymmetrization of C2-Symmetric Dihydroxycyclohexene", J. Org. Chem., vol. 68, pp. 1150-1153, 2003, Wisconsin.

(Continued)

*Primary Examiner* — Sun Jae Yoo
(74) *Attorney, Agent, or Firm* — Grossman, Tucker, Perreault & Pfleger, PLLC

(57) ABSTRACT

Discloses is a process for preparation of a compound of formula 7, or a derivative thereof, wherein $PG^1$ is an alcohol protecting group. Also, disclosed are intermediates and processes for their preparation. The compound of formula 7 can be useful in the preparation of halinchondrin analogs such as Eribulin.

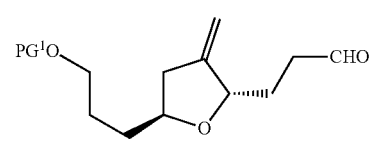

14 Claims, No Drawings

(56) References Cited

OTHER PUBLICATIONS

Jiang et al., "A Novel Route to the F-Ring of Halichondrin B. Diastereoselection in Pd(0)-Mediated meso and C2 Diol Desymmetrization", Organic Letters, vol. 4, No. 20, pp. 3411-3414, 2002, Wisconsin.
Kim et al., "New Syntheses of E7389 C14-C35 and Halichondrin C14-C38 Building Blocks: Double-Inversion Approach", J. Am. Chem. Soc., vol. 131, pp. 15636-15641, 2009, Massachusetts.
KUNZNETSOV et al., "Induction of Morphological and Biochemical Apoptosis following Prolonged Mitotic Blockage by Halichondrin B Macrocyclic Ketone Analog E7389", Cancer Research, vol. 64, pp. 5760-5766, 2004, Japan.
Litaudon et al., "Isohomoalichondrin B, a New Antitumour Polyether Macrolide from the New Zealand Deep-Water Sponge *Lissodendoryx* sp.", Tetrahedron Letters, vol. 35, No. 50, pp. 9435-9438, 1994, New Zealand.
Narayan et al., "Novel second generation analogs of eribulin. Part I: Compounds containing a lipophilic C32 side chain overcome P-glycoprotein susceptibility", Bioorganic & Medicinal Chemistry Letters, vol. 21, pp. 1630-1633, 2011, Massachusetts.
Narayan et al., "Novel second generation analogs of eribulin. Part II: Orally available and active against resistant tumors in vivo", Bioorganic & Medicinal Chemistry Letters, vol. 21, pp. 1634-1638, 2011, Massachusetts.
Narayan et al., "Novel second generation analogs of eribulin. Part III: Blood-brain barrier permeability and in vivo activity in a brain tumor model", Bioorganic & Medicinal Chemistry Letters, vol. 21, pp. 1639-1643, 2011, Massachusetts.
Okouneva et al., "Inhibition of centromere dynamics by eribulin (E7389) during mitotic metaphase", Mol. Cancer Ther., vol. 7, No. 7, pp. 2003-2011, 2008, California.
Rudolph et al., "Early introduction of the amino group to the C27-C35 building block of Eribulin", Tetrahedron Letters, vol. 54, pp. 7059-7061, 2013, Canada.
Sabitha et al., "Synthesis of the C45-053 tetrahydropyran domain of norhalichondrins and the C14-C22 tetrahydrofuran domain of the halichondrin family", RSC Advances, vol. 2, pp. 10157-10159, 2012, India.
Sartillo-Piscil et al., "Diastereoselective synthesis of 1,2-O-isopropylidene-1,6-dioxaspiro[4,4]nonane applying the methodology of generation of radical cations under non-oxidizing conditions", Tetrahedron Letters, vol. 44, pp. 3919-3921, 2003, Mexico.
Sun et al., "Synthesis and Olefination Reactions of an a-Enal from Diacetone Glucose", Communications Synthesis, pp. 28-29, 1982, Maryland.
Trost et al., "Ru-Catalyzed Alkene-Alkyne Coupling. Total Synthesis of Amphidinolide P", J. Am. Chem. Soc., vol. 127, pp. 17921-17937, 2005, California.
Wang et al., "Structure-Activity Relationships of Halichondrin B Analogues: Modifications at C.30-C.38", Bioorganic & Medicinal Chemistry Letters, vol. 10, pp. 1029-1032, 2000, Massachusetts.
Zheng et al., "Macrocyclic ketone analogues of halichondrin B", Bioorganic & Medicinal Chemistry Letters, vol. 14, pp. 5551-5554, 2004, Massachusetts.
International Search Report and Written Opinion from corresponding PCT Appln. No. PCT/CA2012/050859, dated Jan. 29, 2013.
International Search Report and Written Opinion from related PCT Appln. No. PCT/CA2012/050939, dated Feb. 15, 2013.
International Search Report and Written Opinion from related PCT Appln. No. PCT/CA2012/050254, dated Jul. 8, 2013.
International Preliminary Report on Patentability from related PCT Appln. No. PCT/CA2012/050897, dated Jun. 17, 2014.
International Preliminary Report on Patentability from related PCT Appln. No. PCT/CA2012/050939, dated Jul. 1, 2014.
International Search Report from related PCT Appln. No. PCT/CA2014/050504, dated Jul. 24, 2014.
International Search Report and Written Opinion from related PCT Appln. No. PCT/CA2014/050438, dated Jul. 25, 2014.
Office Action from related U.S. Appl. No. 14/361,489 dated Dec. 18, 2014.

* cited by examiner

PROCESS FOR PREPARATION OF 3-((2S,5S)-4-METHYLENE-5-(3-OXOPROPYL)TETRAHYDROFURAN-2-YL)PROPANOL DERIVATIVES AND INTERMEDIATES USEFUL THEREOF

CROSS-REFERENCE TO RELATED APPLICATION

This application is a divisional of U.S. application Ser. No. 14/365,168, filed Jun. 13, 2014 which is a U.S. National Phase Application under 35 U.S.C. §371 of International Patent Application No. PCT/CA2012/050897, filed Dec. 14, 2012, which claims the benefit of and priority to U.S. Provisional patent application No. 61/576,649, filed Dec. 16, 2011. The content of the above-noted patent applications are hereby expressly incorporated by reference into the detailed description hereof.

FIELD

This specification relates to a process for preparation of 3-((2S,5S)-4-methylene-5-(3-oxopropyl)tetrahydrofuran-2-yl)propanol derivatives and intermediates useful thereof.

BACKGROUND

Halinchondrin analogs have been disclosed as having anticancer and antimitotic activity (U.S. Pat. No. 6,214,865, incorporated herein by reference). In particular, Halichondrin B has been reported as a potent anticancer agent that was first isolated from the marine sponge Halichondria okadai (U.S. Pat. No. 6,214,865; WO 2005/118565 A1 and WO 2009/124237 A1, all incorporated herein by reference).

The synthesis of compounds, similar to the compound of formula 7a, has been described by Kishi (*Pure Appl. Chem.* 2003, 75, 1-17; *J. Am. Chem. Soc.* 2009, 131, 15642-15646; *J. Am. Chem. Soc.* 2009, 131, 15636-15641), Phillips (*Angew. Chem., Int. Ed.* 2009, 48, 2346) and Burke (*Org. Lett.* 2002, 4, 3411-3414, *J. Org. Chem.* 2003, 68, 1150-1153), all incorporated herein by reference. However, these methods can be undesirable for commercial manufacturing. For example, all these routes rely on asymmetric reactions that, despite their high degree of selectivity, can give rise to epimers, which are of particular concern in cases where the intended use of the molecule is in the manufacture of an active pharmaceutical ingredient. Furthermore, many of these asymmetric reactions employ chiral ligands that are not necessarily easily commercially available, and which can be a hindrance for large scale production.

There is a need in the art for a process for preparation of 3-((2S,5S)-4-methylene-5-(3-oxopropyl)tetrahydrofuran-2-yl)propanol (7a), and its analogs (7), that can be used in the preparation of halichondrin natural products, its derivatives and analogs, such as, for example and without limitation, eribulin, the compounds described in recent publication of S. Narayan and others (*Bioorganic and Medicinal Chemistry letters*, 2011, 1630-1633; *Bioorganic and Medicinal Chemistry letters*, 2011, 1634-1638, *Bioorganic and Medicinal Chemistry letters*, 2011, 1639-1643), and other eribulin analogs with modified side chains on position C32 of eribulin. In

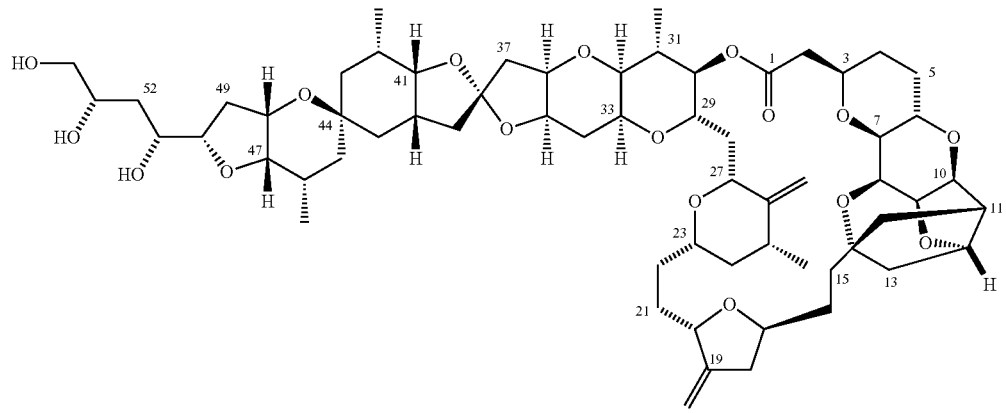

Halichondrin B 2,5-disubstituted (2S,5S)-3-methylene-tetrahydrofurans, such as the compound of formula 7a, can be an important building block for the synthesis of the halichondrin natural products and derivatives, as described in U.S. Pat. Nos. 6,214,865 and 5,436,238, and incorporated herein by reference.

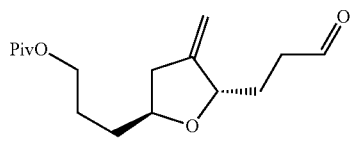

wherein Piv is $(CH_3)_3C-C(=O)-$.

addition, there is a need in the art for a process for preparation of 3-((2S,5S)-4-methylene-5-(3-oxopropyl)tetrahydrofuran-2-yl)prop-1-yl pivaloate (7a), and its analogs (7), that can be prepared from commercially available starting material. Moreover, there is a need in the art for a process for the preparation of 3-((2S,5S)-4-methylene-5-(3-oxopropyl)tetrahydrofuran-2-yl)prop-1-yl pivaloate (7a), and its analogs (7), that can avoid the use of asymmetric reactions, including chiral ligands. In addition, there is a need in the art for a process for preparation of 3-((2S,5S)-4-methylene-5-(3-oxopropyl)tetrahydrofuran-2-yl)prop-1-yl pivaloate (7a), and its analogs (7), where the process is scalable and can lead to a product having high stereochemical purity.

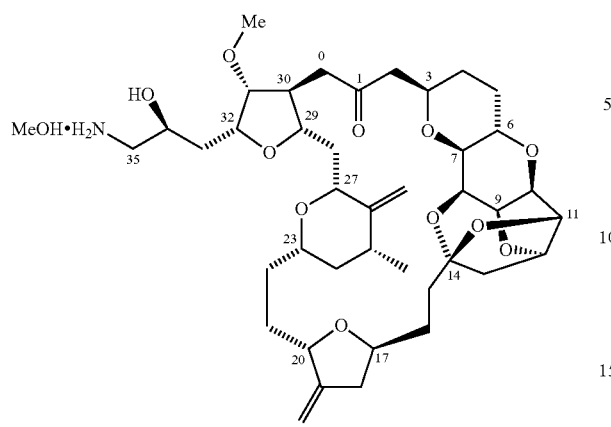

Eribulin mesylate

SUMMARY OF THE INVENTION

In one aspect, the specification discloses a process for preparation of a compound of formula 7, or a derivative thereof, wherein $PG^1$ is an alcohol protecting group,

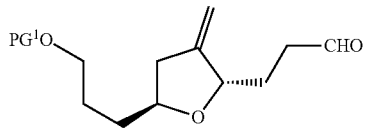

the process comprising:
nucleophillic addition of an allyl-silane derivative of formula 8 to a compound of formula 4 to form the compound of formula 5;

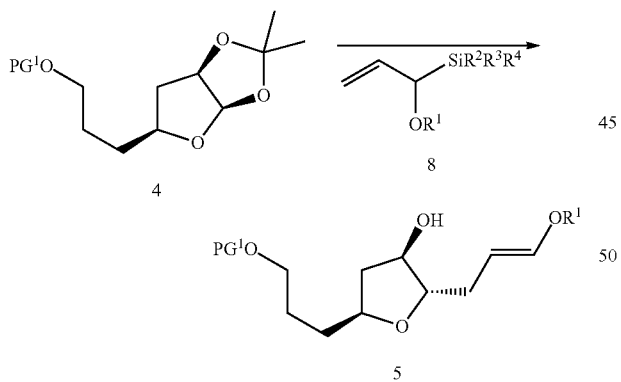

wherein $R^1$ is an alcohol protecting group, and each $R^2$, $R^3$ and $R^4$ independently is an alkyl, cyclo-alkyl, aryl or hetero-aryl group;
deprotecting the compound of formula 5 under conditions to remove the $R^1$ alcohol protecting group, and protecting the resulting aldehyde to form a compound of formula 6, wherein each $R^5$ and $R^6$ independently is an alkyl, cyclo-alkyl, aryl or hetero-aryl group, optionally having one or more heteroatoms, or $R^5$ and $R^6$ together form an alkanediyl group, optionally having one or more heteroatoms;

replacing the hydroxyl group with a methylene in the compound of formula 6, followed by deprotection of the protected aldehyde to form the compound of formula 7;

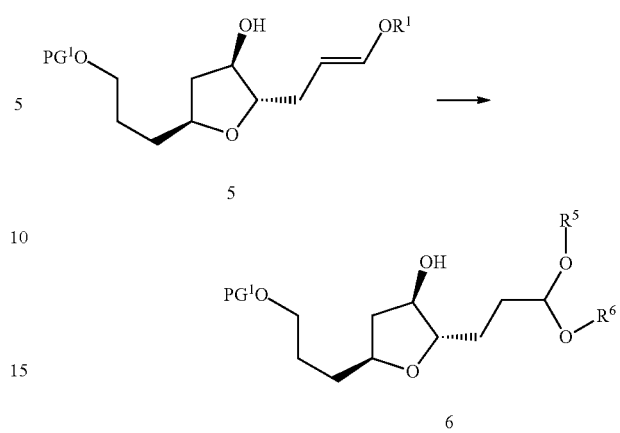

In another aspect, the specification discloses a process for preparation of a compound of formula 7, or a derivative thereof, wherein $PG^1$ is an alcohol protecting group,

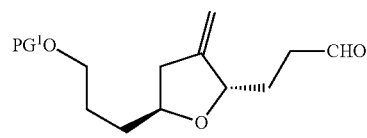

the process comprising:
nucleophillic addition of an allyl-silane derivative of formula 8 to a compound of formula 4 to form the compound of formula 5;

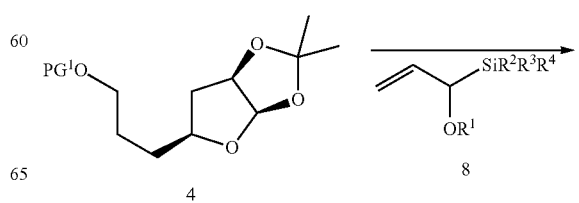

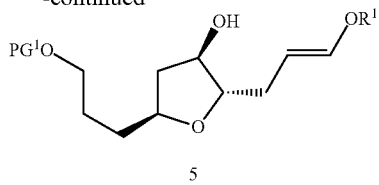

wherein R¹ is a alcohol protecting group, and each R², R³ and R⁴ independently is an alkyl, cyclo-alkyl, aryl or hetero-aryl group;

replacing the hydroxyl group with a methylene group in the compound of formula 5 to form the compound of formula 11; and

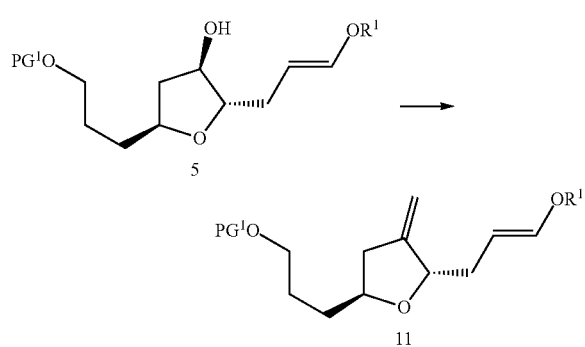

deprotecting the protected aldehyde to remove R¹ and form the compound of formula 7

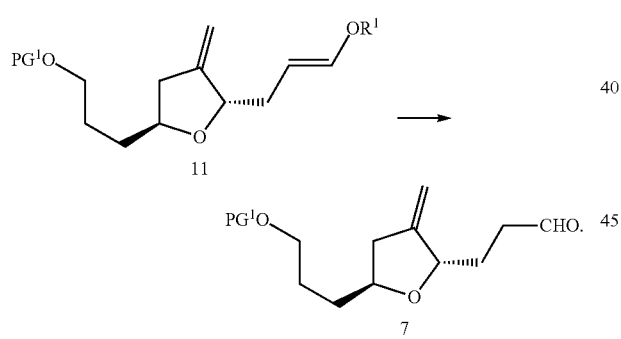

In still another aspect, the specification discloses a compound of formula 4, where PG¹ is an alcohol protecting group.

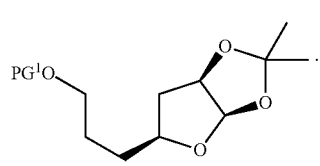

In a further aspect, the specification discloses a compound of formula 5, where G¹ and R¹ each independently is an alcohol protecting group.

In still another aspect, the specification discloses a compound of formula 6,

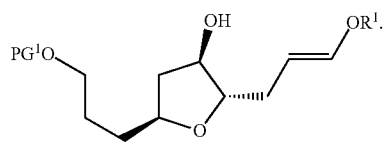

where PG¹ is an alcohol protecting group and R⁵ and R⁶ independently is an alkyl, cyclo-alkyl, aryl or hetero-aryl group, optionally having one or more heteroatoms, or R⁵ and R⁶ together form an alkanediyl group, optionally having one or more heteroatoms.

In another further aspect, the specification discloses compounds of formula 10 and 11, where PG¹ and R¹ each independently is an alcohol protecting group.

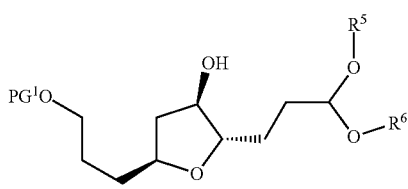

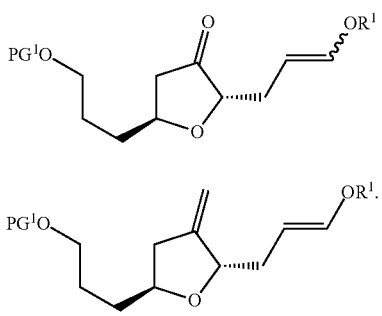

In a still further aspect, the specification discloses a process for the preparation of compounds of formula 4, 5, 6, 10 and 11.

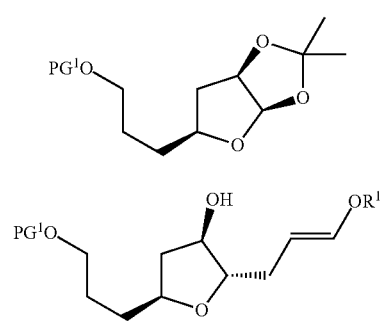

-continued

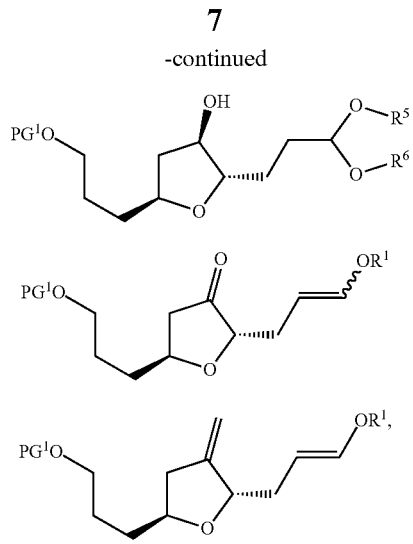

wherein PG$^1$ and R$^1$ (when present) each independently is an alcohol protecting group, and R$^5$ and R$^6$ (when present) independently is an alkyl, cyclo-alkyl, aryl or hetero-aryl group, optionally having one or more heteroatoms, or R$^5$ and R$^6$ together form an alkanediyl group, optionally having one or more heteroatoms.

DESCRIPTION

As described above, in one aspect, the specification discloses a process for preparation of a compound of formula 7, or a derivative thereof, wherein PG$^1$ is an alcohol protecting group,

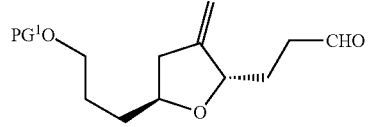

the process comprising:
nucleophillic addition of an allyl-silane derivative of formula 8 to a compound of formula 4 to form the compound of formula 5;

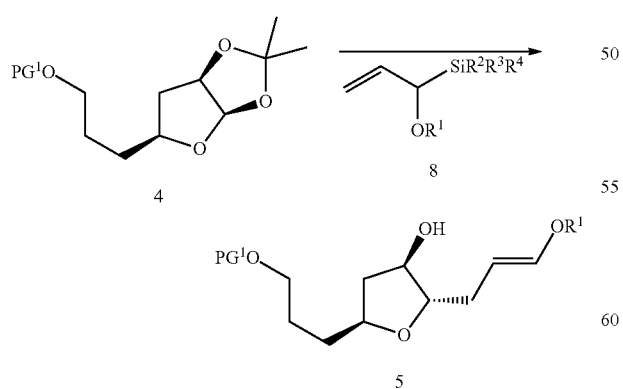

wherein R$^1$ is a alcohol protecting group, and each R$^2$, R$^3$ and R$^4$ independently is an alkyl, cyclo-alkyl, aryl or hetero-aryl group;

deprotecting the compound of formula 5 under conditions to remove the R$^1$ protecting group, and protecting the resulting aldehyde to form a compound of formula 6, wherein each R$^5$ and R$^6$ independently is an alkyl, cyclo-alkyl, aryl or hetero-aryl group, optionally having one or more heteroatoms, or R$^5$ and R$^6$ together form an alkanediyl group, optionally having one or more heteroatoms;

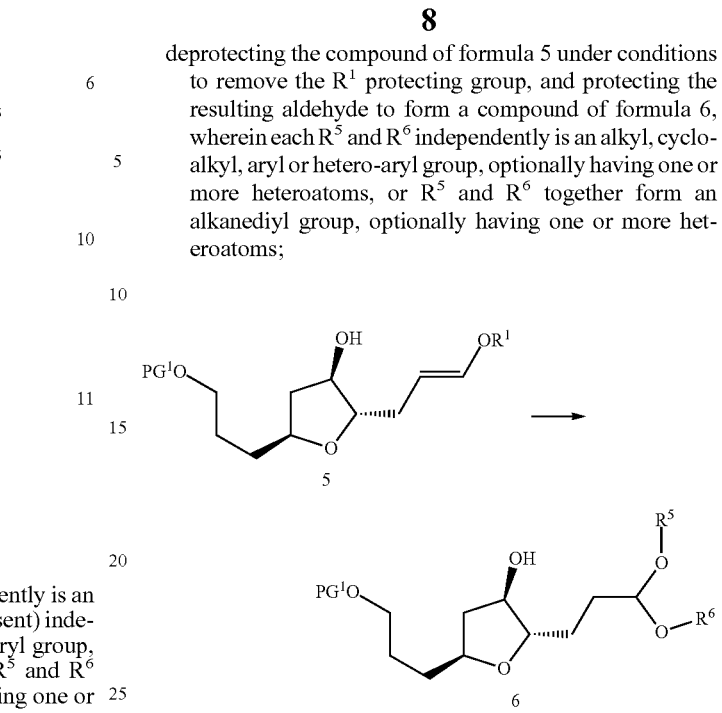

replacing the hydroxyl group with a methylene group in the compound of formula 6, followed by deprotection of the protected aldehyde to form the compound of formula 7;

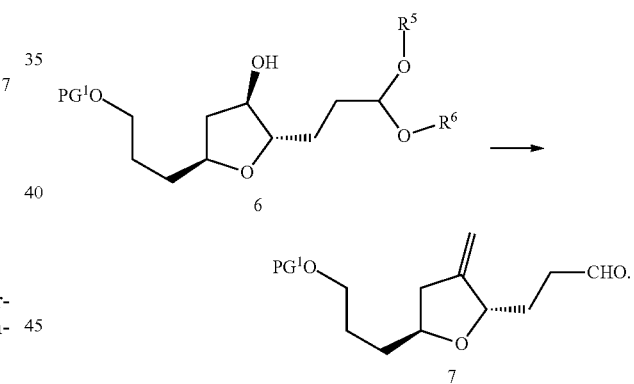

In addition, in another aspect, the specification discloses a process for preparation of a compound of formula 7, or a derivative thereof, wherein PG$^1$ is an alcohol protecting group,

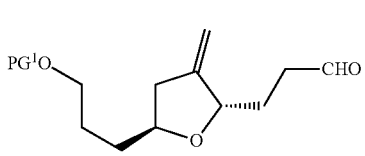

the process comprising:
nucleophillic addition of an allyl-silane derivative of formula 8 to a compound of formula 4 to form the compound of formula 5;

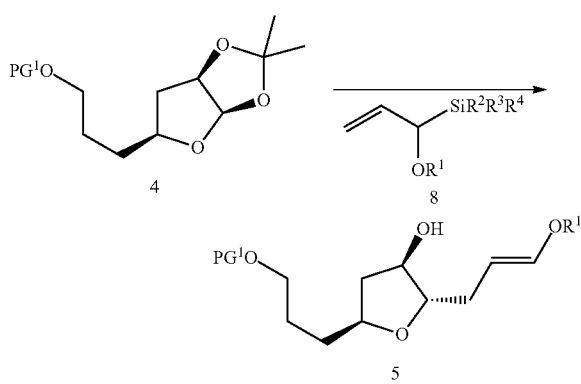

wherein $R^1$ is a alcohol protecting group, and each $R^2$, $R^3$ and $R^4$ independently is an alkyl, cyclo-alkyl, aryl or hetero-aryl group;

replacing the hydroxyl group with a methylene group in the compound of formula 5 to form the compound of formula 11; and

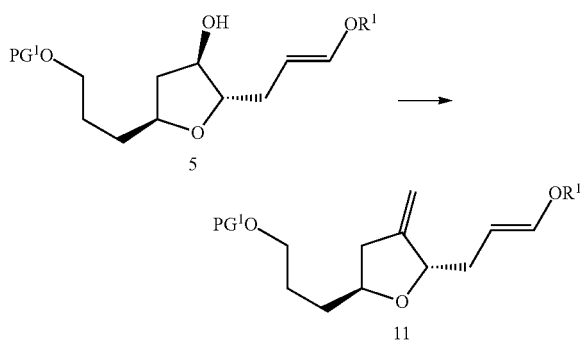

deprotecting the protected aldehyde to remove $R^1$ and form the compound of formula 7

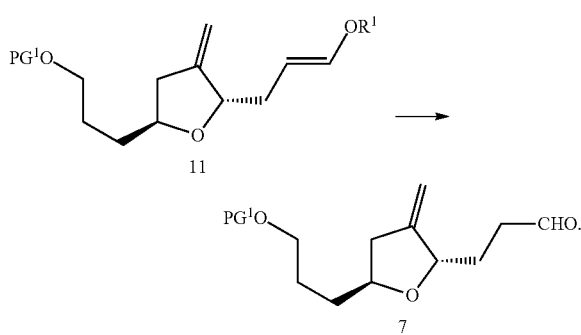

The derivatives of the compound of formula 7 relate to the functionalization of the aldehyde functional group and is not particularly limited. The aldehyde functional group can be replaced by other groups, for example and without limitation, an ester, an amide or an acyl halide.

Without being bound to a particular theory, it is believed that the nucleophilic addition of the allyl-silane derivative of formula 8 utilizes the stereochemical features of the compound of formula 4. In particular, the position of the isopropylidene protecting group on the 1,2-diol facilitates nucleophillic addition from the β-face, i.e. from behind the plane of the page, to form the compound of formula 5 having a trans configuration. Hence, the resulting product obtained can have high stereochemical purity (diastereomeric excess).

The conditions for nucleophillic addition reaction of the compound of formula 4 with the compound of formula 8 are not particularly limited, and can be determined. In one embodiment, for example and without limitation, the nucleophillic addition reaction of the compound of formula 4 with the compound of formula 8 is performed in the presence of an activator. The activator used for such a nucleophillic addition reaction is also not particularly limited, and can be determined. Without being bound by a particular theory, in one embodiment, for example and without limitation, the activator can bind with the oxygen atoms on the compound of formula 4, which can increase the electrophilicity of the anomeric carbon centre on the compound of formula 4 and/or can assist in improving the facial selectivity of nucleophillic attack. In one embodiment, for example and without limitation, the activator is a lewis acid, for instance $BF_3$ or trimethylsilyl triflate (TMSOTf).

The allyl-silane derivative of formula 8 used in the nucleophillic addition reaction is not particularly limited, and should be known to a skilled person, or can be determined. In one embodiment, for example and without limitation, in the allyl-silane derivative of formula 8, $R^1$ is a alcohol protecting group, and each $R^2$, $R^3$ and $R^4$ independently is an alkyl, cyclo-alkyl, aryl or hetero-aryl group. In a further embodiment, for example and without limitation, in the allyl-silane derivative of formula 8, $R^1$ is acetyl, and each $R^2$, $R^3$ and $R^4$ independently is methyl.

The length of the alkyl or alkanediyl group or the number of atoms in the alkyl group, alkanediyl group or the aryl group are not particularly limited, and should be known to a person of skill in the art or can be determined. In one embodiment, for example and without limitation, the alkyl group is a $C_{1-6}$ alkyl. Similar length of alkanediyl groups can also be used, where appropriate. In another embodiment, for example and without limitation, the aryl group is a $C_{6-14}$ aryl.

The term $C_{1-6}$ alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1,2-dimethylbutyl, 1-ethyl-2-methylpropyl, 1,1,2-trimethylpropyl, 1,1-diethyl-2-methylbutyl, 1,1-dimethylbutyl, 2,2-dimethylbutyl, 2-ethylbutyl, 1,3-dimethylbutyl, 2-methylpentyl or 3-methylpentyl.

The term aryl in accordance with the specification is not particularly limited and should be known to a person of skill in the art. The term "aryl" refers to aromatic groups which have at least one ring having a conjugated π-electron system and includes carbocyclic aryl, heterocyclic aryl (also known as heteroaryl groups) and biaryl groups, all of which may be optionally substituted. The aryl groups can include, for example and without limitation, six to fourteen atoms. Examples of aryl group can include, without limitation, phenyl, pyridinyl or naphthyl.

The conditions for the deprotection of the compound of formula 5 or 11 to remove the $R^1$ protecting group is not particularly limited and would depend upon the particular $R^1$ protecting group. In one embodiment, for example and without limitation, the $R^1$ protecting group is an acetyl, and the deprotection is performed, for example and without limitation, in the presence of a base. The type of base used for the deprotection reaction is not particularly limited, and should be known to a skilled worker or can be determined. In one embodiment, for example and without limitation, the base used is a carbonate. In a further embodiment, for example and without limitation, the base is $Na_2CO_3$, $NaHCO_3$ or $K_2CO_3$.

Upon deprotection of the compound of formula 5, an aldehyde is formed, which can be protected to form the compound of formula 6. The protection of the aldehyde is not particularly limited and should be known to a skilled worker or can be determined. In one embodiment, for example and without limitation, an acetal is formed to protect the aldehyde, as shown in the compound of formula 6. The acetal can be formed by reacting with an alcohol. The alcohol used is not particularly limited and can be determined by a skilled worker. In one embodiment, for example and without limitation, the alcohol has one hydroxyl group, is a 1,2-diol or a 1,3-diol. In the compound of formula 6, each $R^5$ and $R^6$ independently is an alkyl, cyclo-alkyl, aryl or hetero-aryl group, optionally having one or more heteroatoms, or $R^5$ and $R^6$ together form an alkanediyl group, optionally having one or more heteroatoms. In a further embodiment, for example and without limitation, the $R^5$ and $R^6$ together form $—CH_2CH_2—$.

As shown above, the compound of formula 6 can be converted into the compound of formula 7 by replacing the hydroxyl group in the compound of formula 6 with a methylene group (similar conversation of compound of formula 5 leads to compound 11, an embodiment of which is shown below in Scheme 2), followed by deprotection of the aldehyde to form the compound of formula 7.

The step of replacing the hydroxyl group in the compound of formula 6 with a methylene group is not particularly limited, and should be known to a skilled worker or can be determined. In one embodiment, for example and without limitation, the hydroxyl group is oxidized to form a ketone (similar conversation of compound of formula 5 leads to compound 10, an embodiment of which is shown below in Scheme 2), followed by conversion of the ketone into an alkene.

The oxidation of the alcohol in the compound of formula 5 or 6 is not particularly limited, and should be known to a skilled worker or can be determined. In one embodiment, for example and without limitation, the oxidation is performed using a chromium-based reagent, such as Collins reagent, pyridinium dichromate (PDC) or pyridinium chlorochromate (PCC); activated dimethyl sulfoxide (DMSO), such as, Swern oxidation, Moffatt oxidation or Doering oxidation; or hypervalent iodine compounds, such as, Dess-Martin periodinane or 2-iodoxybenzoic acid. In a further embodiment, for example and without limitation, the oxidation is performed by Doering oxidation, which uses DMSO and sulfur trioxide-pyridine complex.

Following oxidation of the alcohol in the compound of formula 6 to a ketone, the ketone functional group can be, in one embodiment, for example and without limitation, converted into an alkene (similar conversation of compound of formula 10 leads to compound 11, an embodiment of which is shown below in Scheme 2). The reaction to convert a ketone to an alkene is not particularly limited, and should be known to a skilled worker or can be determined. In one embodiment, for example and without limitation, the ketone is converted to an alkene using Tebbe's reagent, that has the formula $(C_5H_5)_2TiCH_2ClAl(CH_3)_2$. In another embodiment, for example and without limitation, a ketone can be converted into an alkene using the Peterson olefination, the Wittig reaction or the like.

The protecting group $PG^1$ used in the process for the preparation of compound 7 is not particularly limited, and should be known to a skilled worker or can be determined. In one embodiment, for example and without limitation, the protecting group $PG^1$ forms an ester, ether or is a silyl-protecting group. In a further, embodiment for example and without limitation, the ester formed is acetyl (Ac), benzoyl (Bz) or pivaloyl (Piv). In another embodiment, for example and without limitation, the ether protecting group formed is benzyl (Bn), β-methoxyethoxymethyl ether (MEM), trityl (Tr), dimethoxy trityl (DMT), methoxymethyl ether (MOM), or the like. In a still further embodiment, for example and without limitation, the silyl protecting group formed is tert-butyldimethylsilyl (TBDMS), tri-iso-propylsilyloxymethyl (TOM), or triisopropylsilyl (TIPS). In a particular embodiment, for example and without limitation, the protecting group $PG^1$ is Piv.

In one embodiment in accordance with the description, the compound of formula 4 can be obtained from 1,2:5,6-diisopropylidene glucose (compound of formula 1). The compound of formula 1 is derived from a natural sugar and therefore, can be readily available or can be prepared. Further, the compound of formula 1 can be present as a single stereoisomer. In addition, the reactions performed, as disclosed in the specification, can utilize the stereochemical features of the compound of formula 1 to form a single stereoisomer, resulting in products having high stereochemical purity.

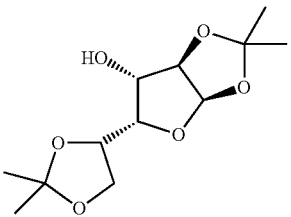

1

In one embodiment, for example and without limitation, the hydroxyl group of the compound of formula 1 is converted into a leaving group (LG), followed by hydrolysis of the 5,6-isopropylidene protecting group and oxidatively cleaving the diol to form the aldehyde of formula 2.

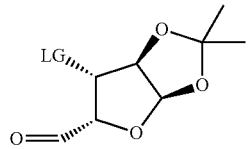

2

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the $pK_a$ of the conjugate acid, with lower $pK_a$ being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is mesylate.

The conditions for hydrolysis of the 5,6-isopropylidene protecting group is not particularly limited, and should be known to skilled worker or can be determined. In one embodiment, for example and without limitation, the 5,6-isopropylidene protecting group is removed using an acid, to yield a diol. The diol can then be oxidatively cleaved to form the aldehyde. The process for oxidative cleavage of the diol is not particularly limited, and should also be known to a skilled worker or can be determined. In one embodiment, for example and without limitation, the oxidative cleavage is performed using periodate oxidation. In a further embodiment, for example and without limitation, the periodate used is $NaIO_4$. The process for conversion of the compound of formula 1 into the compound of formula 2 can also be performed as described in *Synthesis*, 1982, 28-29, incorporated herein by reference.

The compound of formula 2 can undergo an elimination reaction in the presence of a base to remove the leaving group and form an alkene. The alkene obtained can then undergo a Wittig or a Horner-Wadsworth Emmons reaction, by reacting with a $Ph_3P$=$CHCO_2Me$ (9), or analogs thereof, to form the compound of formula 3. The base used for the elimination reaction is not particularly limited and has been described herein above. The analog of the compound of formula 9 is not particularly limited. In one embodiment, for example and without limitation, the phosphonate reagent $(EtO)_2P$(=$O$)—$CH_2CO_2Me$ is used. In another embodiment, for example and without limitation, the methyl group in the ester functionality has been replaced by an alternate alkyl group, such as, for example and without limitation, ethyl, propyl or butyl.

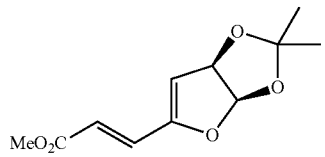

3

The compound of formula 3 can then undergo hydrogenation of the alkene, followed by reduction of the ester functional group to an alcohol, and then protecting the resulting alcohol to form the compound of formula 4.

The conditions for the hydrogenation reaction are not particularly limited and should be known to a skilled worker or can be determined. In one embodiment, for example and without limitation, the hydrogenation reaction is performed using a hydrogenation catalyst, such as for example and without limitation, palladium on carbon (Pd/C). Again in the hydrogenation reaction, and without being bound to a particular theory, it is believed that the presence of the 1,2-isopropylidene group can direct hydrogenation from the β-face, i.e. below the plane of the paper, which can lead to a stereoisomer having the desired stereochemistry, in high diastereomeric excess (d.e.).

The reaction for reduction of an ester to an alcohol is not particularly limited and should be known to a skilled worker or can be determined. In one embodiment, for example and without limitation, reduction is performed using a hydride source. The hydride source used is not particularly limited and should be known to a skilled worker or can be determined. In one embodiment, for example and without limitation, the hydride source is lithium aluminum hydride (LAH), lithium triethylborohydride ($LiEt_3BH$), diisobutylaluminum hydride (DIBALH) or sodium borohydride ($NaBH_4$).

As noted above, using the process disclosed in the specification, compounds having high diastereomeric purity can be obtained. In one embodiment, for example and without limitation, the chiral purity of any one of the compounds of formula 2 to 7 is about 99.0%, 99.1%, 99.2%, 99.3% 99.4%, 99.5%, 99.6%, 99.7%, 99.8%, 99.9% d.e. or any values in between.

In one embodiment, for example and without limitation, the compound of formula 4a can be obtained from the compound of formula 1, according to the Scheme 1, shown below.

Scheme 1: Schematic representation of a process for preparation of compound of formula 4a.

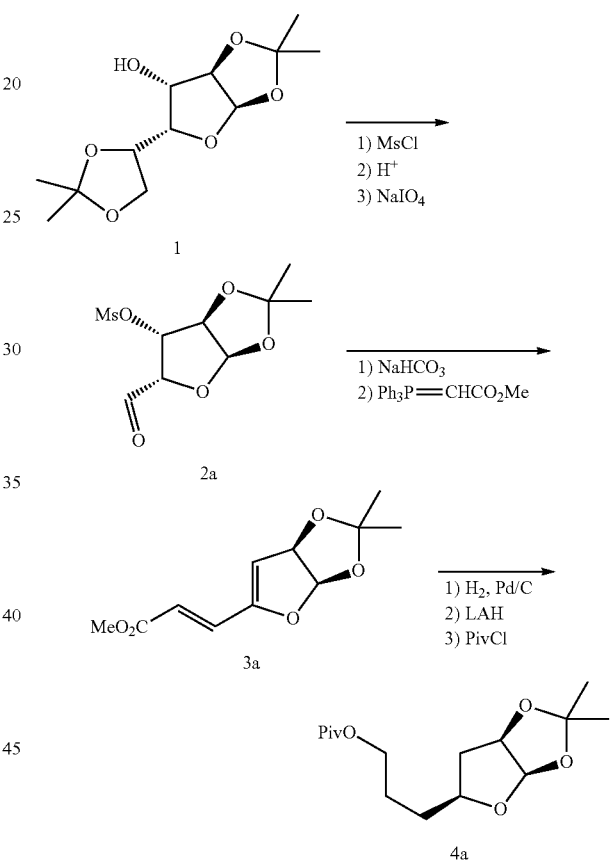

In another embodiment, for example and without limitation, the compound of formula 7a can be obtained from the compound of formula 4a, according to Scheme 2, shown below.

Scheme 2: Schematic representation of a process for preparation of a compound of formula 7a.

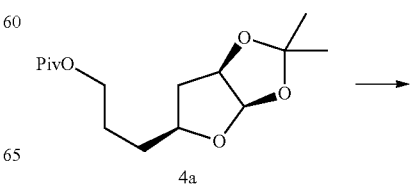

-continued

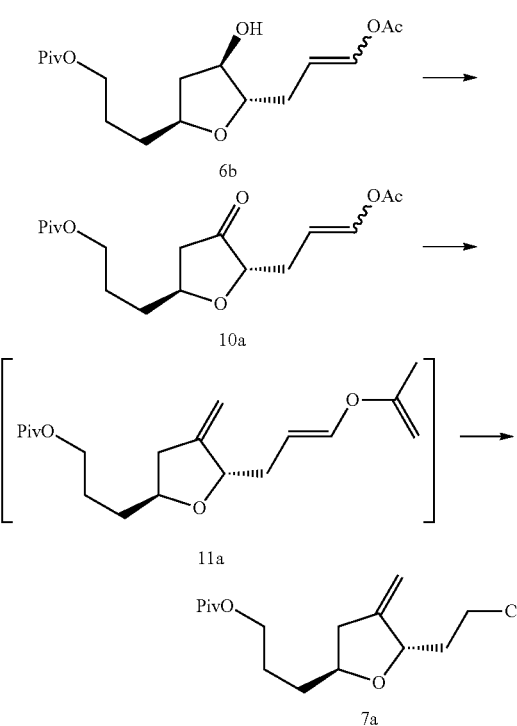

In a further particular embodiment, for example and without limitation, the compound of formula 7a can be obtained from the compound of formula 4a, according to Scheme 3, shown below.

Scheme 3: Schematic representation of a process for preparation of a compound of formula 7a, where PPTS = pyridinium para-toluene sulfonate and TMS = trimethylsilyl.

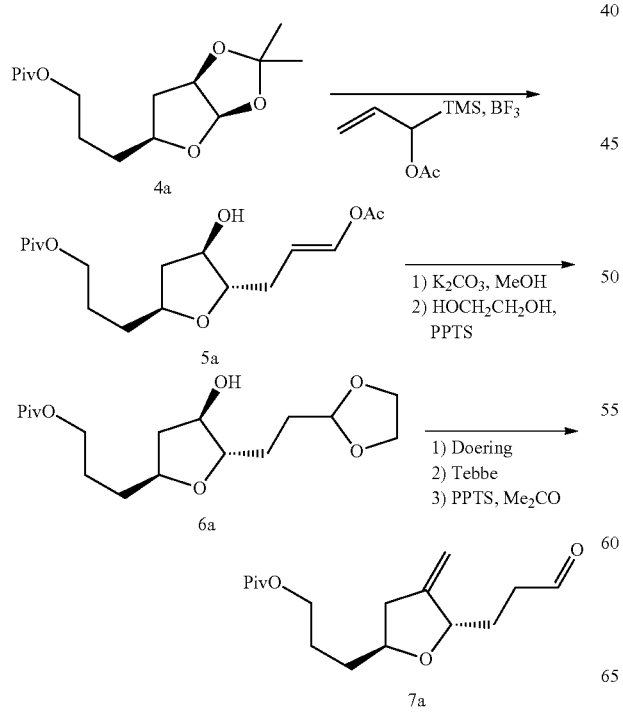

EMBODIMENTS

1. A process for preparation of a compound of formula 7, or a derivative thereof, wherein $PG^1$ is an alcohol protecting group,

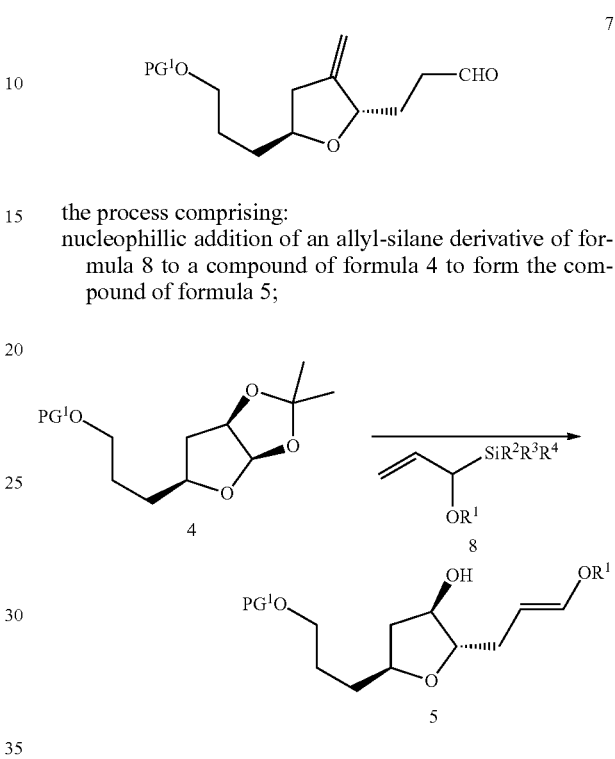

the process comprising:
nucleophillic addition of an allyl-silane derivative of formula 8 to a compound of formula 4 to form the compound of formula 5;

wherein $R^1$ is a alcohol protecting group, and each $R^2$, $R^3$ and $R^4$ independently is an alkyl, cyclo-alkyl, aryl or hetero-aryl group;
deprotecting the compound of formula 5 under conditions to remove the $R^1$ protecting group, and protecting the resulting aldehyde to form a compound of formula 6, wherein each $R^5$ and $R^6$ independently is an alkyl, cyclo-alkyl, aryl or hetero-aryl group, optionally having one or more heteroatoms, or $R^5$ and $R^6$ together form an alkanediyl group, optionally having one or more heteroatoms;

replacing the hydroxyl group with a methylene group in the compound of formula 6, followed by deprotection of the protected aldehyde to form the compound of formula 7;

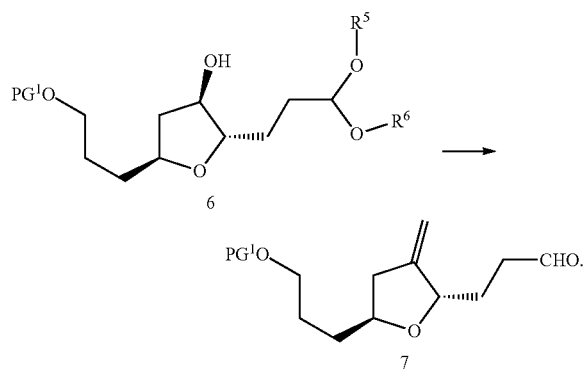

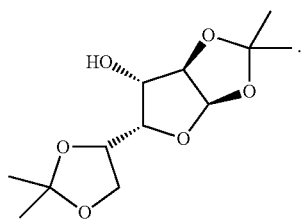

2. The process according to embodiment 1, wherein $PG^1$, the oxygen to which it is attached and the propanol derivative together form an ester.

3. The process according to embodiment 1, wherein $PG^1$ is a pivaloyl group.

4. The process according to any one of embodiments 1 to 3, wherein $R^1$, the oxygen to which it is attached and the allylsilane derivative together form an ester.

5. The process according to any one of embodiments 1 to 3, wherein $R^1$ is an acetyl group.

6. The process according to any one of embodiments 1 to 5, wherein each $R^2$, $R^3$ and $R^4$ independently is a $C_{1-6}$ alkyl, $C_{6-14}$ aryl or $C_{5-14}$ hetero-aryl group.

7. The process according to any one of embodiments 1 to 5, wherein each $R^2$, $R^3$ and $R^4$ independently is a methyl group.

8. The process according to any one of embodiments 1 to 7, wherein the nucleophillic addition reaction is performed in the presence of an activator.

9. The process according to embodiment 8, wherein the activator is boron trifluoride.

10. The process according to any one of embodiments 1 to 9, wherein hydrolysis of the compound of formula 5 is performed using a base.

11. The process according to embodiment 10, wherein the base is $K_2CO_3$.

12. The process according to any one of embodiments 1 to 11, wherein each $R^5$ and $R^6$ together form an alkanediyl group.

13. The process according to any one of embodiments 1 to 11, wherein each $R^5$ and $R^6$ together form $-CH_2CH_2-$.

14. The process according to any one of embodiments 1 to 13, wherein the compound of formula 6 is converted to the compound of formula 7 by oxidizing the alcohol to a ketone, followed by substituting the oxygen by a methylene group.

15. The process according to embodiment 14, wherein the oxidation is performed by the Doering oxidation reaction.

16. The process according to embodiment 14 or 15, wherein the substitution reaction is performed by use of Tebbe's reagent.

17. The process according to any one of embodiments 1 to 16, wherein the deprotection of the protected aldehyde to form the compound of formula 7, is performed using an acid.

18. The process according to embodiment 14, wherein the mild acid is pyridinium para-toluene sulfonate (PPTS).

19. The process according to any one of embodiments 1 to 18, wherein the compound of formula 4 is formed from the compound of formula 1

20. The process according to embodiment 19, wherein the compound of formula 4 is obtained by:

converting the hydroxyl group of compound of formula 1 into a leaving group (LG), hydrolyzing the 5,6-isopropylidene protecting group and oxidatively cleaving the diol to form the aldehyde of formula 2;

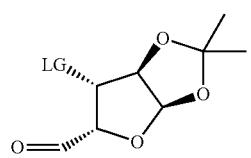

reacting the compound of formula 2 with a base to eliminate the leaving group (LG), followed by reacting the resulting alkene with $Ph_3P=CHCO_2Me$ (9), or an analog thereof, to form the compound of formula 3;

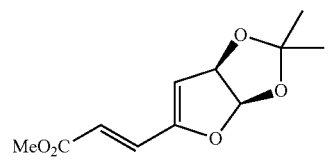

hydrogenating the alkene, reducing the ester functional group to an alcohol and protecting the resulting alcohol to form the compound of formula 4.

21. The process according to embodiment 20, wherein the leaving group formed is a sulfonate based leaving group.

22. The process according to embodiment 20, wherein the leaving group formed is a mesylate.

23. The process according to any one of embodiments 20 to 22, wherein hydrolysis of the 5,6-isopropylidene protecting group of the compound of formula 1 is performed using an acid.

24. The process according to any one of embodiments 20 to 23, wherein the oxidative cleavage of the diol obtained from the compound of formula 1 is performed by periodate oxidation.

25. The process according to any one of embodiments 20 to 23, wherein the oxidative cleavage of the diol obtained from the compound of formula 1 is performed by sodium periodate.

26. The process according to any one of embodiments 20 to 25, wherein the base for the elimination reaction is $NaHCO_3$.

27. The process according to any one of embodiments 20 to 26, wherein the hydrogenation of the compound of formula 3 is performed using Palladium on carbon catalyst and hydrogen gas.

28. The process according to any one of embodiments 20 to 26, wherein the reduction of the ester functional group is performed using a hydride source.

29. The process according to embodiment 28, wherein the hydride source is lithium aluminum hydride.

30. The process according to any one of embodiments 20 to 29, wherein the protection of the alcohol group to form the compound of formula 4 is performed using pivaloyl chloride.

31. The compound of formula 4

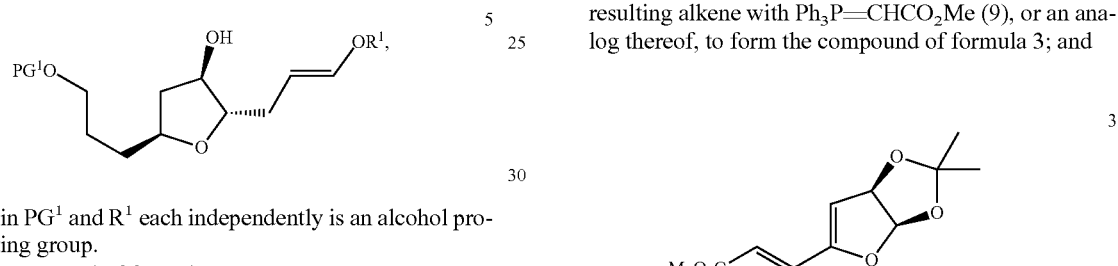

wherein $PG^1$ is an alcohol protecting group.

32. The compound of formula 5

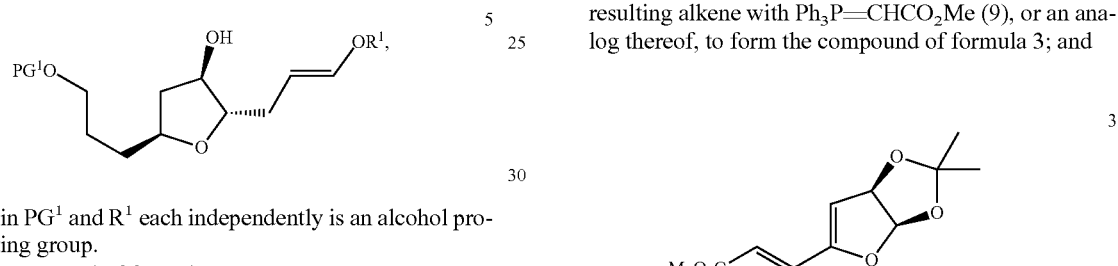

wherein $PG^1$ and $R^1$ each independently is an alcohol protecting group.

33. The compound of formula 6

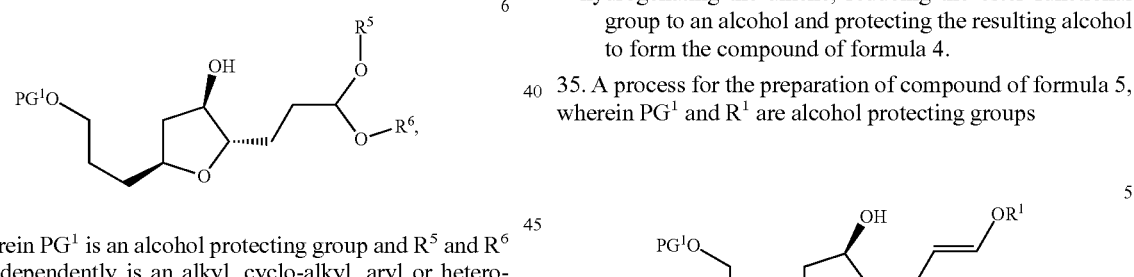

wherein $PG^1$ is an alcohol protecting group and $R^5$ and $R^6$ independently is an alkyl, cyclo-alkyl, aryl or heteroaryl group, optionally having one or more heteroatoms, or $R^5$ and $R^6$ together form an alkanediyl group, optionally having one or more heteroatoms.

34. A process for the preparation of compound of formula 4, where $PG^1$ is an alcohol protecting group,

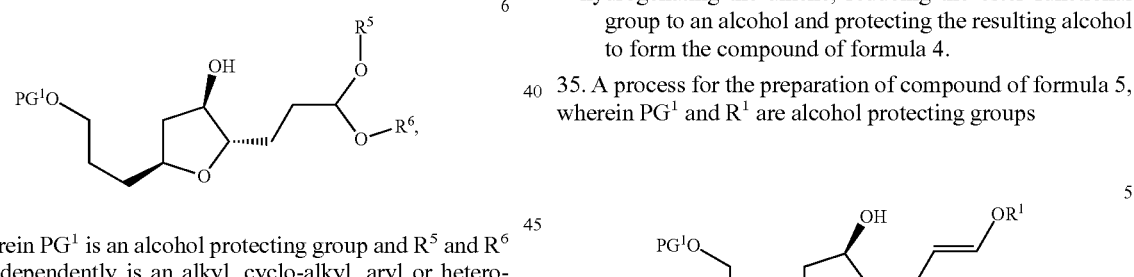

the process comprising:
converting the hydroxyl group of compound of formula 1 into a leaving group, hydrolyzing the 5,6-isopropylidene protecting group and oxidatively cleaving the diol to form the aldehyde of formula 2;

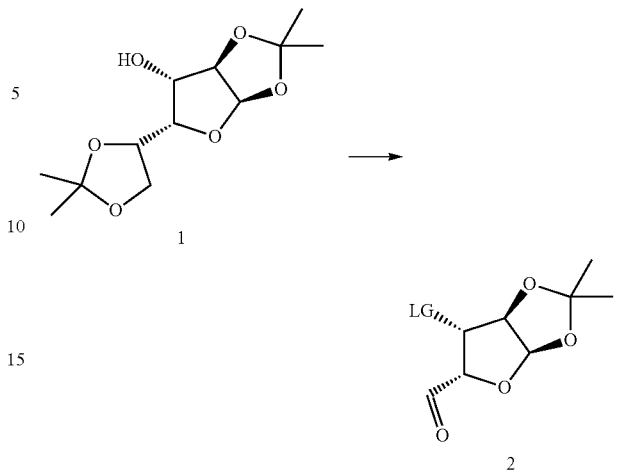

reacting the compound of formula 2 with a base to eliminate the leaving group (LG), followed by reacting the resulting alkene with $Ph_3P=CHCO_2Me$ (9), or an analog thereof, to form the compound of formula 3; and

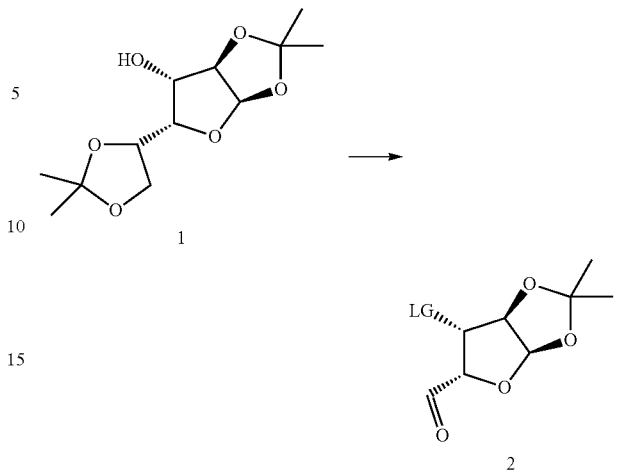

hydrogenating the alkene, reducing the ester functional group to an alcohol and protecting the resulting alcohol to form the compound of formula 4.

35. A process for the preparation of compound of formula 5, wherein $PG^1$ and $R^1$ are alcohol protecting groups

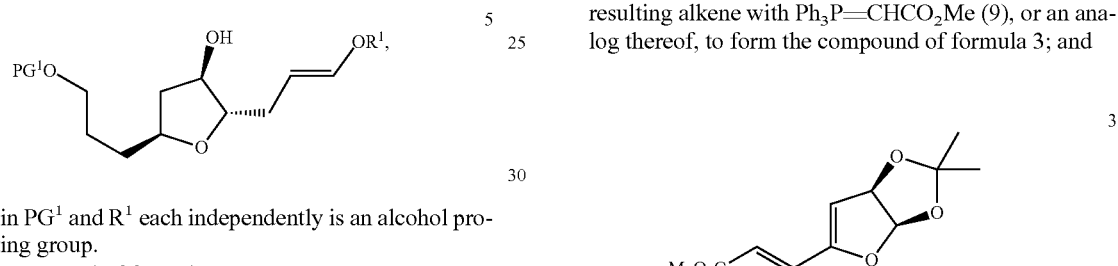

the process comprising:
the process as defined in embodiment 34; and
nucleophillic addition of an allyl-silane derivative of formula 8 to a compound of formula 4 to form the compound of formula 5;

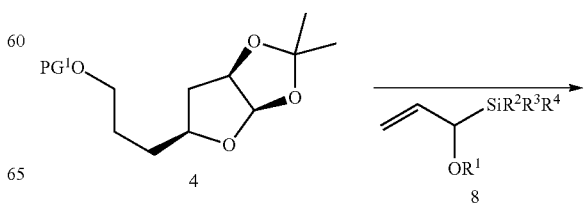

-continued

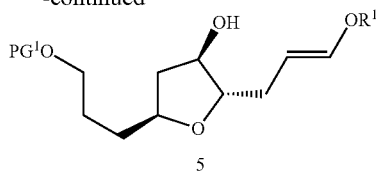

5 wherein $R^1$ is a alcohol protecting group, and each $R^2$, $R^3$ and $R^4$ independently is an alkyl, cyclo-alkyl, aryl or hetero-aryl group.

36. A process for preparation of compound of formula 6,

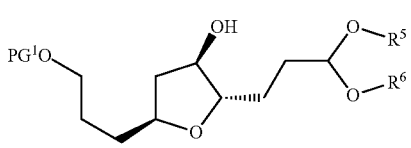

6 the process comprising:
the process as defined in embodiment 35; and
hydrolyzing the compound of formula 5 under conditions to remove the $R^1$ protecting group, and protecting the resulting aldehyde to form a compound of formula 6, wherein each $R^5$ and $R^6$ independently is an alkyl, cyclo-alkyl, aryl or hetero-aryl group, optionally having one or more heteroatoms, or $R^5$ and $R^6$ together form an alkanediyl group, optionally having one or more heteroatoms.

37. A process for the preparation of compound of formula 5, wherein $PG^1$ and $R^1$ are alcohol protecting groups

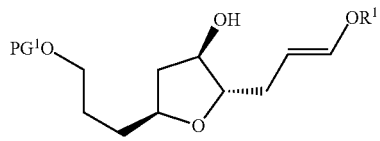

5 the process comprising:
nucleophillic addition of an allyl-silane derivative of formula 8 to a compound of formula 4 to form the compound of formula 5;

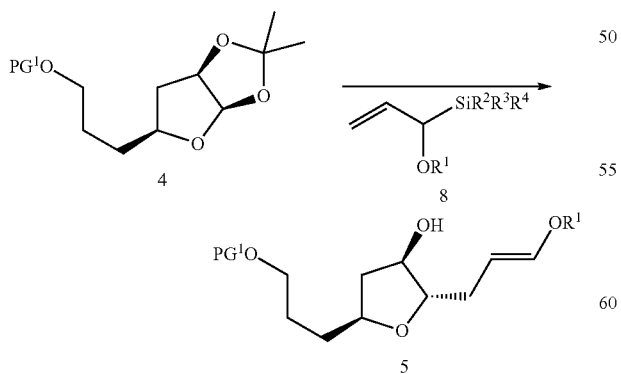

wherein $R^1$ is a alcohol protecting group, and each $R^2$, $R^3$ and $R^4$ independently is an alkyl, cyclo-alkyl, aryl or hetero-aryl group.

38. A process for preparation of compound of formula 6,

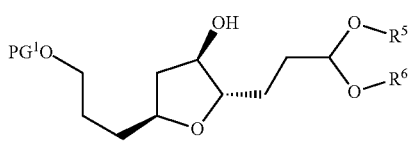

6 the process comprising:
hydrolyzing the compound of formula 5 under conditions to remove the $R^1$ protecting group, and protecting the resulting aldehyde to form a compound of formula 6, wherein each $R^5$ and $R^6$ independently is an alkyl, cyclo-alkyl, aryl or hetero-aryl group, optionally having one or more heteroatoms, or $R^5$ and $R^6$ together form an alkanediyl group, optionally having one or more heteroatoms.

39. A process for preparation of a compound of formula 7, or a derivative thereof, wherein $PG^1$ is an alcohol protecting group,

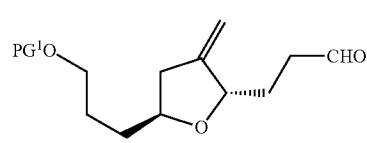

7 the process comprising:
nucleophillic addition of an allyl-silane derivative of formula 8 to a compound of formula 4 to form the compound of formula 5;

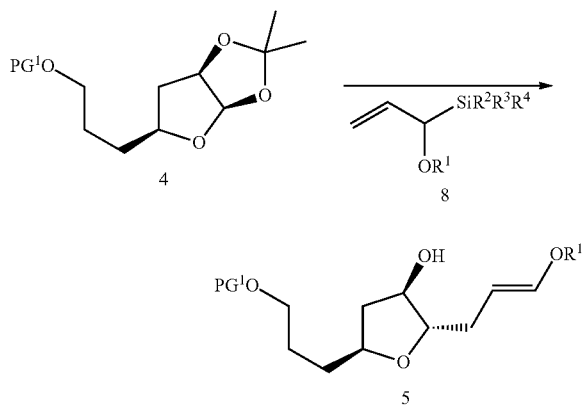

wherein $R^1$ is a alcohol protecting group, and each $R^2$, $R^3$ and $R^4$ independently is an alkyl, cyclo-alkyl, aryl or hetero-aryl group;
replacing the hydroxyl group with a methylene group in the compound of formula 5 to form the compound of formula 11; and

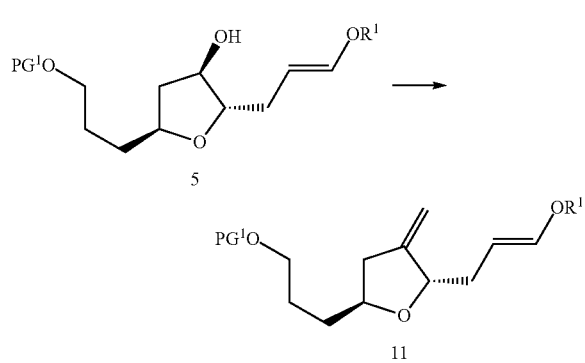

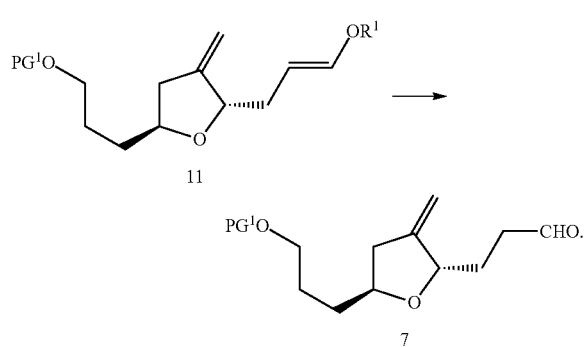

deprotecting the protected aldehyde to remove R¹ and form the compound of formula

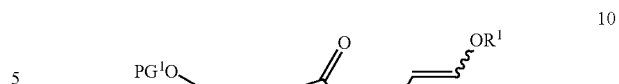

40. The process according to embodiment 39, wherein PG¹, the oxygen to which it is attached and the propanol derivative together form an ester.

41. The process according to embodiment 39, wherein PG¹ is a pivaloyl group.

42. The process according to any one of embodiments 39 to 41, wherein R¹, the oxygen to which it is attached and the allyl-silane derivative together form an ester.

43. The process according to any one of embodiments 39 to 41, wherein R¹ is an acetyl group.

44. The process according to any one of embodiments 39 to 43, wherein each $R^2$, $R^3$ and $R^4$ independently is a $C_{1-6}$ alkyl, $C_{6-14}$ aryl or $C_{5-14}$ hetero-aryl group.

45. The process according to any one of embodiments 39 to 43, wherein each $R^2$, $R^3$ and $R^4$ independently is a methyl group.

46. The process according to any one of embodiments 39 to 45, wherein the nucleophillic addition reaction is performed in the presence of an activator.

47. The process according to embodiment 46, wherein the activator is boron trifluoride.

48. The process according to any one of embodiments 39 to 47, wherein the compound of formula 5 is converted to the compound of formula 11 by oxidizing the alcohol to a ketone, followed by substituting the oxygen by a methylene group.

49. The process according to embodiment 48, wherein the oxidation is performed by the Doering oxidation reaction.

50. The process according to embodiment 48 or 49, wherein the substitution reaction is performed by use of Tebbe's reagent.

51. The compound of formula 10

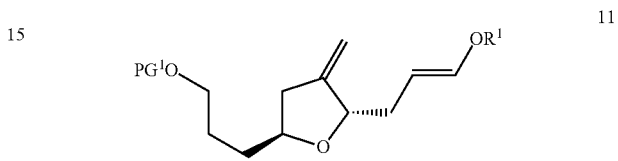

wherein PG¹ and R¹ each independently is an alcohol protecting group.

52. The compound of formula 11

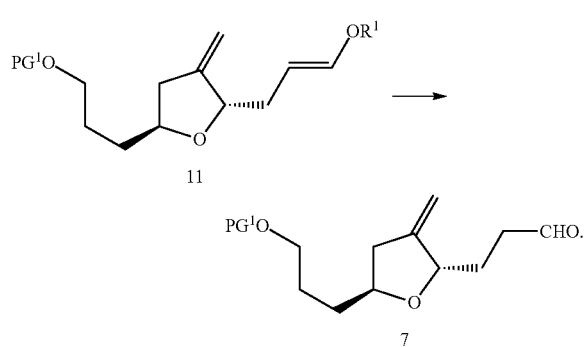

wherein PG¹ and R¹ each independently is an alcohol protecting group.

53. A process for the preparation of compound of formula 10, wherein PG¹ and R¹ each independently is an alcohol protecting group, the process comprising oxidation of the compound of formula 5 to form the compound of formula 10

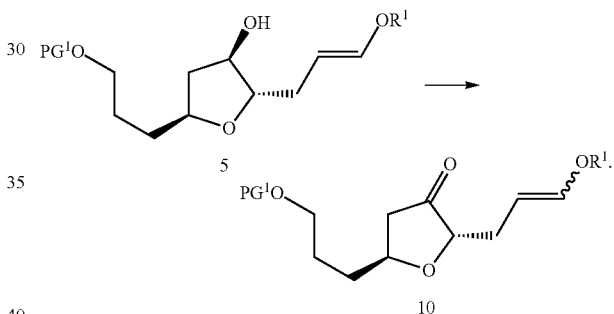

54. The process according to embodiment 53, wherein the compound of formula 5 is obtained according to the process as defined in embodiment 35 or 37.

55. A process for preparation of a compound of formula 11, wherein PG¹ and R¹ each independently is an alcohol protecting group, the process comprising replacing the ketone with a methylene group in the compound of formula 10 to form the compound of formula 11

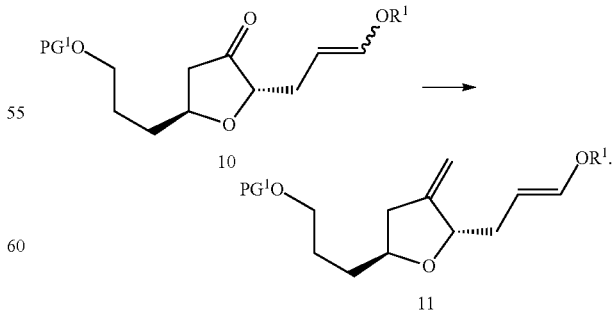

56. The process according to embodiment 55, wherein the compound of formula 10 is obtained according to the process as defined in embodiment 53 or 54.

57. A process for preparation of a halichondrin analog, comprising the process as defined in any one of embodiments 1-30 and 34-56.

58. A process for preparation of Eribulin, comprising the process as defined in any one of embodiments 1-30 and 34-56.

EXAMPLES

The following examples are illustrative and non-limiting, and represent specific embodiments of the present invention.

The compound of formula 2a can be prepared as described in *Synthesis* 1982, 28-29, incorporated herein by reference.

Example 1

Preparation of Compound of Formula 3a

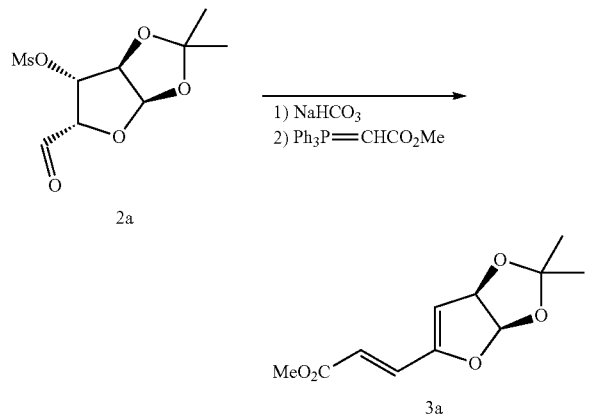

Compound 2a (1 wt. parts) was dissolved in a mixture of methanol (4.6 vol. parts) and water (1.8 vol. parts). NaHCO₃ (0.6 wt. parts) was added and the mixture heated to reflux until reaction was complete by Thin Layer Chromatography (TLC). The mixture was cooled to ambient and methyl triphenylphosphoranylidene acetate (1.14 wt. parts) was added. After stirring for 0.5 hr, the reaction mixture was quenched with water and extracted 2 times with methyl t-butyl ether (MTBE). The combined organic extract was dried over Na₂SO₄, filtered and concentrated under vacuum to give a residue. The residue was triturated with methyl t-butyl ether (3.6 vol. parts), filtered and rinsed with methyl t-butyl ether. The filtrate was concentrated to give compound 3a (1.2 wt. parts) as a mixture of cis/trans-isomers.

Example 2

Preparation of Compound of Formula 4a

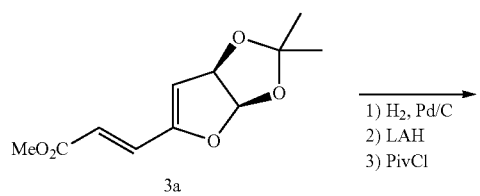

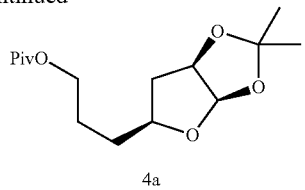

A solution of compound 3a (1 wt. parts), dissolved in i-PrOH (20 vol. parts) was added to 10 wt/wt % palladium on carbon (Pd/C) (0.4 wt. parts) in a Parr hydrogenation flask. The reaction vessel was pressurized to 40 psi with hydrogen and maintained at this pressure, while being agitated for 20 hours. Following this, the reaction mixture was filtered through a plug of celite, which was then rinsed with methanol (MeOH) (25 vol. parts). The combined filtrate and MeOH rinse was concentrated under reduced pressure to yield a viscous oil. This crude product was then dissolved in diethylether (Et₂O) (40 vol. parts), set stirring, and cooled in an ice bath. LiAlH₄ (2 eq., 0.34 wt. parts) was then added portionwise. After complete addition, the ice bath was removed and the reaction mixture was allowed to warm to room temperature over the course of 3 hours. The slurry was then quenched by the slow addition of water (0.34 vol. parts), aqueous 1N NaOH (0.34 vol. parts), and then more water (1.02 vol. parts), followed by a period of stirring (20 minutes). Na₂SO₄ was then added to remove excess water. After filtering off the solids, and concentrating the filtrate under reduces pressure, the resultant crude oil was dissolved in pyridine (18 vol. parts), set stirring, and cooled in an ice bath under a nitrogen (N₂ (g)) atmosphere. To the mixture was added pivaloyl chloride (PivCl) (1.7 eq., 0.9 wt. parts), and the reaction was left to warm to ambient temperature over a period of 20 hours. Following this, the contents of the reaction flask were poured onto water (40 vol. parts) and stirred for 1 hour. This mixture was then extracted with CH₂Cl₂ (3 times 20 vol. parts). The combined extracts were washed with NaHCO₃, followed by brine, and dried over Na₂SO₄. After filtering and concentration under reduced pressure, the crude oil was subjected to column chromatography (stationary phase: SiO2, eluent: 1:1 Heptanes:EtOAc) to yield compound 4a (0.4 eq.) as a colorless oil.

Example 3

Preparation of Compound of Formula 6a

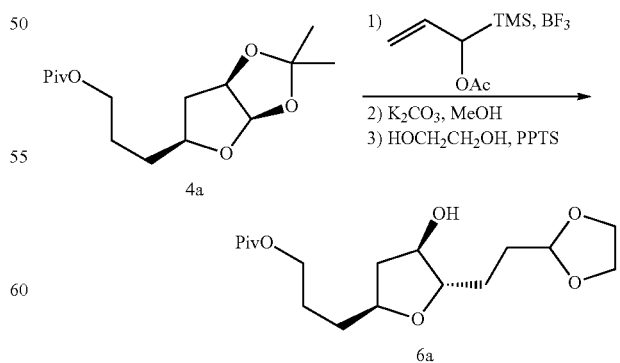

Compound 4a (1 wt. parts) and 1-(acetyloxy)-1-(trimethylsilyl)-2-propene (3.0 eq., 1.8 wt. parts) were dissolved in anhydrous dichloroethane (DCE) (4 vol. parts) under nitrogen ($N_2$(g)). While cooling the reaction vessel in an ice water bath, $BF_3OEt_2$ (4.6 eq., 2.3 wt. parts) was added in a dropwise fashion. The reaction mixture was then left to warm to room temperature over 20 hours. Following this, the reaction mixture was diluted with ethyl acetate (EtOAc) (120 vol. parts), washed with saturated aqueous $NaHCO_3$, and then concentrated under reduced pressure. The residue was then dissolved in MeOH (4 vol. parts). A solution of $K_2CO_3$ (0.6 eq., 0.3 wt. parts) dissolved in water (4 vol. parts) was then added, and the resulting mixture was stirred vigorously for 30 minutes. After dilution with EtOAc (120 vol. parts) and washing with brine until the washings are neutral (pH 7 by pH paper), the organic phase was dried over $Na_2SO_4$, filtered, and concentrated under reduced pressure. The crude residue was then treated with 0.3 wt. parts of ethylene glycol (1.5 eq.), and with 0.06 wt. parts of pyridinium para-toluene sulfonate (PPTS) (0.07 eq.),) in toluene (10 vol. parts) at reflux for 1 hour. Following this, the crude residue obtained by concentrating the reaction mixture under reduced pressure, was directly applied to the top of a silica gel column, and eluted with ethyl acetate (EtOAc). Fractions containing the product were collected and concentrated to dryness to yield compound 6a (0.24 eq.) as a yellow oil.

Example 4

Preparation of Compound of Formula 6b

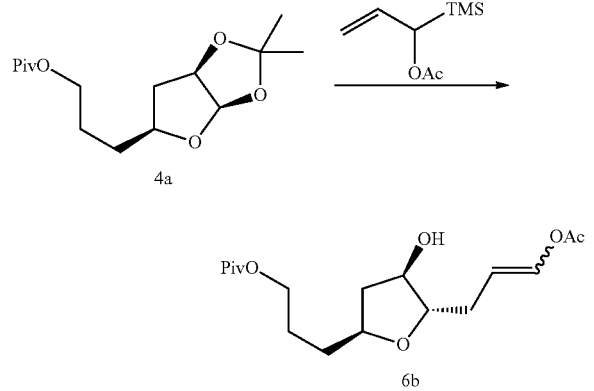

Compound 4a (1 eq.) and 1-(acetyloxy)-1-(trimethylsilyl)-2-propene (3.0 eq.) were dissolved in anhydrous dichloroethane (DCE) (12 vol. parts) under nitrogen ($N_2$ (g)). The internal temperature of this solution was maintained at 0° C. and $BF_3OEt_2$ (4.6 eq.) was added in a dropwise fashion. Stirring was continued at 0° C. for 6 h. Following this, the reaction was quenched by the slow addition of aqueous sodium bicarbonate solution (40 vol. parts) at 0° C. and then warming to room temperature. Once the evolution of gas had ceased, the layers were separated, and the aqueous phase was extracted with ethyl acetate (3 times 40 vol. parts). The combined organic extracts were dried over $Na_2SO_4$, filtered, and then concentrated under reduced pressure. Purification of the crude residue via column chromatography, (stationary phase: $SiO_2$, eluent: 1:1 heptanes:EtOAc), afforded (0.5 wt. parts, 44% yield) of compound 6b as a light yellow oil.

Example 5

Preparation of Compound of Formula 10a

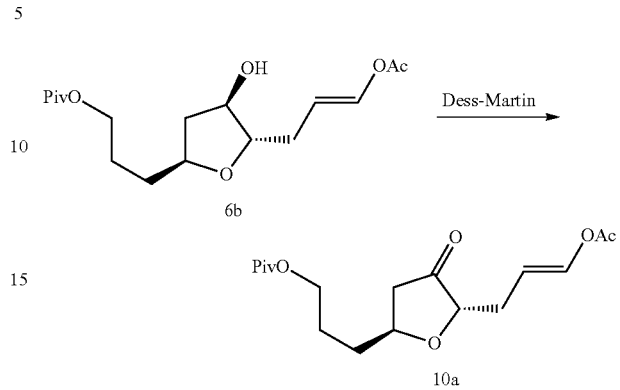

Compound 6b (1 eq.) was dissolved in dichloromethane (DCM) (15 vol.). To this solution was then added Dess-Martin periodinane reagent (1.5 eq.). After stirring at ambient temperature for 20 hours, the reaction mixture was concentrated. The resulting residue was triturated with methyl t-butyl ether (MTBE), the solids were removed by filtration, and the filtrate concentrated under reduced pressure. Further purification was achieved by passing the crude product through a silica plug and eluting with 1:1 heptane:EtOAc. This produced (0.87 wt. parts, 87% yield) of ketone 10a.

Example 6

Preparation of compound of formula 7a

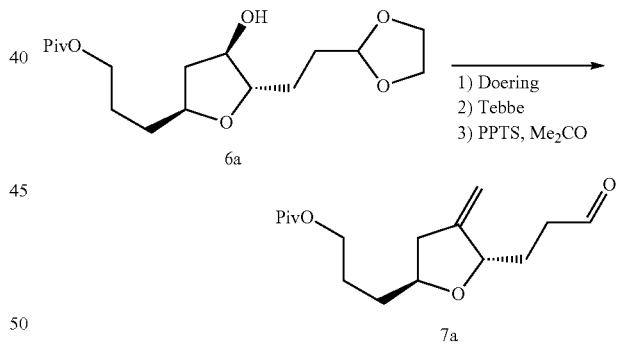

In an appropriately sized reaction vessel, pyridine-sulfur trioxode complex (3.1 eq., 1.5 wt. parts) was dissolved in anhydrous dimethylsulfoxide (DMSO) (5.9 vol. parts) under nitrogen ($N_2$). After stirring for 10 minutes, triethylamine ($NEt_3$) (3.9 eq., 1.2 wt. parts) was added followed by a solution of 6a (1 wt. parts) dissolved in anhydrous DMSO (8.7 vol. parts) which was added dropwise over the course of 30 minutes. The reaction mixture was left to stir for 1 hour, and then diluted with dietylehter ($Et_2O$) (440 vol. parts), washed with water, brine, and dried over $Na_2SO_4$. Filtration and concentration provided a yellow oil which was passed through a silica plug, eluting with 1:1 heptanes:EtOAc. The resulting colorless oil was then dissolved and set stirring in anhydrous tetrahydrofuran (THF) (5.9 vol. parts) in an appropriately sized nitrogen ($N_2$(g)) purged flask. To this solution was added a 0.5M solution of Tebbe's reagent in toluene (0.85 eq., 5.0 vol. parts). The dark red reaction mixture was left to stir for 30 minutes. The reaction mixture was diluted with diethylether (Et$_2$O) (60 vol. parts), 10 drops of 0.1N NaOH were added, followed by Na$_2$SO$_4$ and the slurry was stirred for a further 20 minutes. Filtration through celite to remove the solids, followed by passage through a plug of silica eluting with 1:1 Heptanes:EtOAc and concentration under reduced pressure yielded an oil which was used directly for the next step. A solution of pyridinium para-toluene sulfonate (PPTS) (0.4 eq., 0.3 wt. parts) dissolved in acetone (26 vol. parts) and water (2.9 vol. parts) was added to the crude residue, and then heated to reflux for 20 hours. The reaction mixture was diluted with EtOAc (440 vol. parts), washed with saturated aqueous NaHCO$_3$ followed by brine, dried over Na$_2$SO$_4$, filtered and concentrated under reduced pressure. Purification by column chromatography (stationary phase: SiO$_2$, eluent: 1:1 heptanes:EtOAc) provided compound 7a (0.034 eq.) as a colorless oil.

Example 7

Preparation of Compound of Formula 7a from 10a

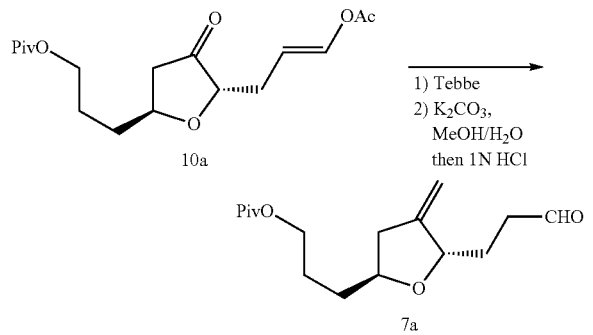

A solution of compound 10a (1 eq.), dissolved in anhydrous THF (8 vol. parts), was cooled to 0° C. To this mixture was slowly added Tebbe's reagent (1.3 eq., 0.5M in toluene) using a cannula. The resulting dark red solution was stirred at 0° C. for 45 minutes. Once complete disappearance of the staring material had been observed by TLC, the reaction was diluted with MTBE (20 vol. parts), quenched by slow addition of aqueous 0.1N NaOH (2.5 vol. parts) at 0° C., and then allowed to warm to room temperature within approximately 1 hour. The brown/orange suspension was filtered through a plug of silica, concentrated under reduced pressure, triturated with pentane, filtered through a disposable frit, and then concentrated again. MeOH (6.5 vol. parts) was added followed by saturated aqueous K$_2$CO$_3$ (6.5 vol. parts), and the resulting biphasic slurry was stirred rapidly for 20 minutes. TLC analysis indicated complete hydrolysis of the acetate-enolether at this point. In order to hydrolyze the vinyl-enolether (formed by reaction of the Tebbe reagent with the carbonyl group of the enol-acetate) the reaction flask was cooled in an ice bath while concentrated HCl (4 vol. parts) was slowly added. After complete hydrolysis of both the enol-acetate and the vinyl-enolether, the mixture of free aldehyde and methoxy-hemiacetal was concentrated to approximately half the initial volume on the rotary evaporator. Tetrahydrofuran (THF) (13 vol. parts) was added, and the mixture was again concentrated. This was repeated two more times. The resulting acidic aqueous solution was neutralized with aqueous NaHCO$_3$, and extracted with EtOAc (3 times 8 vol. parts). The organic extracts were combined, rinsed with brine, dried over Na$_2$SO$_4$, filtered, and concentrated under reduced pressure. Purification by column chromatography (stationary phase: SiO$_2$, eluent: 7:3 heptane:EtOAc) afforded compound 7a (0.23 wt. parts, 25% yield) as a light yellow oil.

Certain adaptations and modifications of the described embodiments can be made. Therefore, the above discussed embodiments are considered to be illustrative and not restrictive.

What is claimed is:

1. A process for the preparation of compound of formula 4, where PG$^1$ is an alcohol protecting group,

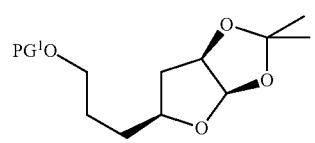

the process comprising:
    converting the hydroxyl group of compound of formula 1 into a leaving group (LG), hydrolyzing the 5,6-isopropylidene protecting group and oxidatively cleaving the diol to form the aldehyde of formula 2;

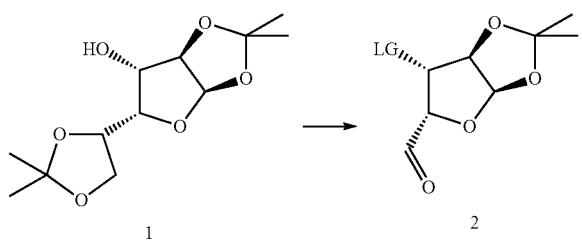

reacting the compound of formula 2 with a base to eliminate the leaving group (LG), followed by reacting the resulting alkene with Ph$_3$P=CHCO$_2$Me (9), or an analog thereof, to form the compound of formula 3; and

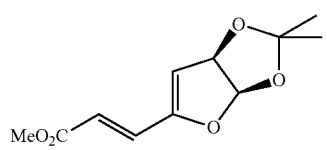

hydrogenating the alkene, reducing the ester functional group to an alcohol and protecting the resulting alcohol to form the compound of formula 4.

2. The process according to claim 1, wherein the leaving group (LG) formed is a sulfonate based leaving group.

3. The process according to claim 1, wherein the leaving group (LG) formed is a mesylate.

4. The process according to claim 1, wherein hydrolysis of the 5,6-isopropylidene protecting group of the compound of formula 1 is performed using an acid.

5. The process according to claim 2, wherein hydrolysis of the 5,6-isopropylidene protecting group of the compound of formula 1 is performed using an acid.

6. The process according to claim 1, wherein the oxidative cleavage of the diol obtained from the compound of formula 1 is performed by periodate oxidation.

7. The process according to claim 5, wherein the oxidative cleavage of the diol obtained from the compound of formula 1 is performed by periodate oxidation.

8. The process according to claim 1, wherein the oxidative cleavage of the diol obtained from the compound of formula 1 is performed by sodium periodate.

9. The process according to claim 1, wherein the base for the elimination reaction is $NaHCO_3$.

10. The process according to claim 1, wherein the hydrogenation of the compound of formula 3 is performed using Palladium on carbon catalyst and hydrogen gas.

11. The process according to claim 1, wherein the reduction of the ester functional group is performed using a hydride source.

12. The process according to claim 11, wherein the hydride source is lithium aluminum hydride.

13. The process according to claim 1, wherein the protection of the alcohol group to form the compound of formula 4 is performed using pivaloyl chloride.

14. A process for preparation of Eribulin, comprising the process as defined in claim 1.

* * * * *